United States Patent
Emgenbroich

(10) Patent No.: US 11,198,800 B2
(45) Date of Patent: Dec. 14, 2021

(54) CONTROL OF ADHESIVE DOMAINS

(71) Applicants: LTS LOHMANN Therapie-Systeme AG, Andernach (DE); DOW SILICONES CORPORATION, Midland, MI (US)

(72) Inventor: Marco Emgenbroich, Rheinbach (DE)

(73) Assignees: LTS LOHMANN Therapie-Systeme AG, Andernach (DE); DOW SILICONES CORPORATION, Midland, MI (US)

( * ) Notice: Subject to any disclaimer, the term of this patent is extended or adjusted under 35 U.S.C. 154(b) by 213 days.

(21) Appl. No.: 16/318,430

(22) PCT Filed: Jul. 19, 2017

(86) PCT No.: PCT/EP2017/068212
§ 371 (c)(1),
(2) Date: Jan. 17, 2019

(87) PCT Pub. No.: WO2018/015424
PCT Pub. Date: Jan. 25, 2018

(65) Prior Publication Data
US 2020/0071571 A1 Mar. 5, 2020

(30) Foreign Application Priority Data

Jul. 22, 2016 (EP) ..................... 16180813

(51) Int. Cl.
| | |
|---|---|
| *C09J 7/38* | (2018.01) |
| *A61K 9/70* | (2006.01) |
| *C08G 77/06* | (2006.01) |
| *C08G 77/20* | (2006.01) |
| *C08G 77/382* | (2006.01) |
| *C08G 77/442* | (2006.01) |
| *C09J 11/06* | (2006.01) |
| *C09J 183/04* | (2006.01) |
| *C09J 183/10* | (2006.01) |

(52) U.S. Cl.
CPC ............ *C09J 7/385* (2018.01); *A61K 9/7069* (2013.01); *C08G 77/06* (2013.01); *C08G 77/20* (2013.01); *C08G 77/382* (2013.01); *C08G 77/442* (2013.01); *C09J 11/06* (2013.01); *C09J 183/04* (2013.01); *C09J 183/10* (2013.01)

(58) Field of Classification Search
CPC .. C09J 2483/00; C09J 2433/00; C09J 183/04; C09J 7/385; C09J 183/10
See application file for complete search history.

(56) References Cited

U.S. PATENT DOCUMENTS

| | | | |
|---|---|---|---|
| 2006/0078604 A1* | 4/2006 | Kanios | A61K 47/32 424/449 |
| 2012/0114737 A1 | 5/2012 | Loubert et al. | |
| 2016/0003036 A1 | 1/2016 | Mickael | |
| 2016/0030362 A1* | 2/2016 | Liao | A61K 31/4168 424/448 |
| 2020/0179298 A1* | 6/2020 | Mohr | A61K 31/407 |
| 2020/0261394 A1* | 8/2020 | Emgenbroich | A61K 9/7069 |

FOREIGN PATENT DOCUMENTS

| | | | |
|---|---|---|---|
| CN | 101356247 A | 1/2009 | |
| EP | 2599847 A1 | 6/2013 | |
| WO | WO-2010124187 A2 * | 10/2010 | ............ C09J 183/04 |
| WO | WO-2016130408 A1 * | 8/2016 | ............ A61K 31/167 |

OTHER PUBLICATIONS

International Search Report and Written Opinion for International Application No. PCT/EP2017/068212, European Patent Office, Netherlands, dated Sep. 19, 2017, 8 pages.

* cited by examiner

*Primary Examiner* — Mark S Kaucher
(74) *Attorney, Agent, or Firm* — Sterne, Kessler, Goldstein & Fox P.L.L.C.

(57) ABSTRACT

A method of inverting the phase arrangement of the silicone phase and the acrylic phase in a silicone acrylic hybrid composition, the silicone acrylic hybrid composition comprising: a) a silicone acrylic hybrid pressure sensitive adhesive, and b) a solvent, wherein the phase arrangement of the silicone phase and the acrylic phase in the initial silicone acrylic hybrid composition forming a continuous external phase and a discontinuous internal phase is determined by the solvent, comprising the step of adding an activator to the silicone acrylic hybrid composition, wherein the activator a) is liquid at 20° C. and 1013 mbar, b) has a boiling point which is higher than the boiling point of the solvent and/or has a vapor pressure at 20° C. which is lower than the vapor pressure of the solvent contained in the silicone acrylic hybrid composition, and c) provides better dissolution properties for the inner phase of the initial silicone acrylic hybrid composition than the solvent contained in the silicone acrylic hybrid composition.

18 Claims, No Drawings

CONTROL OF ADHESIVE DOMAINS

TECHNICAL FIELD OF THE INVENTION

The present invention relates to a method of inverting the phase arrangement of the silicone phase and the acrylic phase in a silicone acrylic hybrid composition, a method of preparing a pressure sensitive adhesive film or layer based on a silicone acrylic hybrid composition, and a transdermal drug delivery system comprising such a pressure sensitive adhesive film or layer.

BACKGROUND OF THE INVENTION

Pressure sensitive adhesives (PSAs) are known in the art and are commercially available. Some of the more common types of PSAs are formulations based on acrylates, silicone, natural rubbers, and synthetic rubbers. These PSAs are typically formulated for end use and find utility in a wide variety of applications including transdermal drug delivery systems (TDDSs).

Common classes of pressure sensitive adhesives used in TDDSs include silicone-based and acrylate-based PSAs.

Acrylate-based PSAs, also referred to as acrylate PSAs, are broadly used in TDDSs due to the fact that they are relatively low in cost when compared to other PSAs and solubilize many types of functional drugs for TDDSs. TDDSs using acrylate-based PSAs usually provide good adhesion properties. The disadvantages of acrylate-based PSAs include poor high temperature performance, poor low temperature performance, inability to adhere to surfaces with low surface energies, and the potential to build excessive adhesion to the skin in medical tape applications which can result in painful removal for the user and skin irritation. Silicone-based PSAs, also referred to as silicone PSAs, are typically produced by either blending or condensing together a silicone resin and a silicone polymer, such as polydimethylsiloxane (PDMS). Silicone materials by nature are very stable at high temperatures and the low glass transition temperature (Tg) of PDMS (less than −115° C.) ultimately provides a PSA that can find use in temperatures ranging from −100° C. to 265° C. Silicone-based PSAs also have excellent chemical inertness, electrical insulating properties, biocompatibility, and the ability to adhere to low surface energy substrates such as silicone release liners, polytetrafluoroethylene, and fluorohalocarbon materials. In TDDSs the silicone-based PSAs generally provide a higher drug flux and a higher active agent utilization compared to acrylate-based PSAs. Usually no interaction between the active agent and the silicone groups occurs. The primary disadvantage of silicone-based PSAs is their high cost compared to other technologies. Other limitations include lower tack and limited adhesion build (when necessary) in comparison to acrylate-based PSAs. Further, the addition of functional excipients is often necessary in order to dissolve and stabilize the active agent.

In the manufacturing of TDDSs polymer blends have been utilized containing both acrylate PSAs and silicone PSAs to combine the advantages of both technologies. Physical blends of PSA may provide better wear adhesion and drug permeation properties. However, physical blends may be subject to phase separation. As is known in the art, phase separation is generally caused by the incompatibility of two dissimilar materials, such as in the simple example of oil and water. In this particular case, the lower surface energy of the silicone PSA becomes incompatible with the higher surface energy of the acrylate PSA and phase separation occurs.

The class of silicone acrylic (SilAc) hybrid pressure sensitive adhesives overcomes the non-compatibility of the acrylate PSAs and the silicone PSAs. A SilAc hybrid PSA include the product of a chemical reaction between a silicon-containing pressure sensitive adhesive composition comprising acrylate or methacrylate functionality, an ethylenically unsaturated monomer, and an initiator (i.e. in the presence of an initiator). Examples of such SilAc hybrid PSAs and methods of making such hybrid compositions are disclosed, for example, in EP 2 599 847 A1. SilAc hybrid PSAs show improved compatibility compared to physical blends of silicone and acrylic PSA materials. For healthcare applications the PSAs are provided in solvents acceptable for pharmaceutical use. PSAs used in the manufacturing of TDDSs are typically supplied in n-heptane or ethyl acetate. The straight-chain alkane n-heptane is also referred to throughout as "heptane". Examples of SilAc hybrid PSA compositions include the PSA series 7-6100 and 7-6300 manufactured and supplied in n-heptane or ethyl acetate by Dow Corning.

It was found that, depending on the solvent in which the SilAc hybrid PSA is supplied, the arrangement of the silicone phase and the acrylic phase providing a silicone or acrylic continuous external phase and a corresponding discontinuous internal phase is different. If the SilAc hybrid composition is supplied in n-heptane, the composition contains a continuous, silicone external phase and a discontinuous, acrylic internal phase. If the SilAc hybrid composition is supplied in ethyl acetate, the composition contains a continuous, acrylic external phase and a discontinuous, silicone internal phase.

Thus, using an ethyl acetate-based SilAc hybrid composition in a method of preparing a pressure sensitive adhesive film or layer by coating the composition on a film or release liner and drying said coated composition results in the provision of a pressure sensitive adhesive film or layer with an external acrylic phase.

If it is intended to prepare a pressure sensitive adhesive film or layer based on a SilAc hybrid PSA with an external silicone phase to take advantage, for example, of the better skin compatibility properties of the silicone PSA or expected higher diffusion rates in a continuous silicone phase for several active agents, a SilAc hybrid composition based on n-heptane would be necessary. However, if an active agent should be included in the pressure sensitive adhesive film or layer which is not compatible with n-heptane, problems in the manufacturing process may arise due to the poor solubility of the active agent. In such cases an unstable product, for example, a pressure sensitive adhesive film or layer wherein the active agent is undissolved or which recrystallizes during storage is produced. On the other hand, taking advantage of the ethyl acetate-based SilAc hybrid composition in terms of its better dissolution properties for the active agent, an easier incorporation of potential further excipients which mostly are compatible with ethyl acetate but not with n-heptane such as polyvinylpyrrolidone or methacrylates, and an easier manufacturing process would always result in a pressure sensitive adhesive film or layer with a continuous, acrylic external phase. Similar issues may arise when the ingredients of the film are more compatible with the solvent n-heptane and an external acrylate phase is desired. However, only a few ingredients are compatible with n-heptane, such as silicone oils or lipophilic enhancers.

There remains a need for a method to control the phase arrangement of the silicone phase and the acrylic phase in SilAc hybrid compositions and a method of preparing a pressure sensitive adhesive film or layer based on a SilAc hybrid composition wherein the phase arrangement of the continuous external phase and the discontinuous internal phase of a silicone acrylic hybrid composition can be adjusted by the process of preparation.

OBJECTS AND SUMMARY OF THE INVENTION

It is an object of certain embodiments of the present invention to provide a method to adjust the phase arrangement of the silicone phase and the acrylic phase in a silicone acrylic hybrid composition.

It is an object of certain embodiments of the present invention to provide a method to invert the phase arrangement of the silicone phase and the acrylic phase in a silicone acrylic hybrid composition.

It is an object of certain embodiments of the present invention to provide a method of preparing a pressure sensitive adhesive film or layer based on a silicone acrylic hybrid composition wherein the phase arrangement of the silicone phase and the acrylic phase of the used silicone acrylic hybrid composition can be adjusted by the process of preparation.

It is an object of certain embodiments of the present invention to provide a pressure sensitive adhesive film or layer based on a silicone acrylic hybrid composition wherein the phase arrangement of the silicone phase and the acrylic phase was adjusted during the process of preparation.

It is an object of certain embodiments of the present invention to provide a pressure sensitive adhesive film or layer based on a silicone acrylic hybrid composition, wherein the continuous external phase and the discontinuous internal phase were adjusted to improve the stability of the film or layer and to improve the release of the active agent contained therein.

It is an object of certain embodiments of the present invention to provide a transdermal drug delivery system comprising a pressure sensitive adhesive film or layer, wherein the continuous external phase and the discontinuous internal phase are adjusted to improve the stability of transdermal drug delivery system and to improve the release of the active agent contained therein.

These objects and others are accomplished by the present invention, which according to one aspect relates to a method of inverting the phase arrangement of the silicone phase and the acrylic phase in a silicone acrylic hybrid composition,
the silicone acrylic hybrid composition comprising:
a) a silicone acrylic hybrid pressure sensitive adhesive, and
b) a solvent, wherein the phase arrangement of the silicone phase and the acrylic phase in the initial silicone acrylic hybrid composition forming a continuous external phase and a discontinuous internal phase is determined by the solvent,
comprising the step of adding an activator to the silicone acrylic hybrid composition, wherein the activator
a) is liquid at 20° C. and 1013 mbar,
b) has a boiling point which is higher than the boiling point of the solvent and/or has a vapor pressure at 20° C. which is lower than the vapor pressure of the solvent contained in the silicone acrylic hybrid composition, and
c) provides better dissolution properties for the inner phase of the initial silicone acrylic hybrid composition than the solvent contained in the silicone acrylic hybrid composition.

According to one specific aspect, the invention relates to a method of inverting the phase arrangement of the silicone phase and the acrylic phase in a silicone acrylic hybrid composition,
the silicone acrylic hybrid composition comprising:
a) a silicone acrylic hybrid pressure sensitive adhesive, and
b) ethyl acetate, wherein the phase arrangement of the silicone phase and the acrylic phase in the initial silicone acrylic hybrid composition forming a continuous, acrylic external phase and a discontinuous, silicone internal phase is determined by ethyl acetate,
comprising the step of adding an activator to the silicone acrylic hybrid composition, preferably in an amount of at least 10% of the total solvent volume contained in the silicone acrylic hybrid composition, wherein the activator
a) is liquid at 20° C. and 1013 mbar,
b) has a boiling point which is higher than the boiling point of ethyl acetate and/or has a vapor pressure at 20° C. which is lower than the vapor pressure of ethyl acetate, and
c) provides better dissolution properties for the inner phase of the initial silicone acrylic hybrid composition than the ethyl acetate.

According to one specific other aspect, the invention relates to a method of inverting the phase arrangement of the silicone phase and the acrylic phase in a silicone acrylic hybrid composition,
the silicone acrylic hybrid composition comprising:
a) a silicone acrylic hybrid pressure sensitive adhesive, and
b) n-heptane, wherein the phase arrangement of the silicone phase and the acrylic phase in the initial silicone acrylic hybrid composition forming a continuous, silicone external phase and a discontinuous, acrylic internal phase is determined by n-heptane,
comprising the step of adding an activator to the silicone acrylic hybrid composition, preferably in an amount of at least 10% of the total solvent volume contained in the silicone acrylic hybrid composition, wherein the activator
a) is liquid at 20° C. and 1013 mbar,
b) has a boiling point which is higher than the boiling point of n-heptane and/or has a vapor pressure at 20° C. which is lower than the vapor pressure of n-heptane, and
c) provides better dissolution properties for the inner phase of the initial silicone acrylic hybrid composition than the n-heptane.

According to one aspect, the invention relates to a method of preparing a pressure sensitive adhesive film or layer based on a silicone acrylic hybrid composition comprising the steps of:
i) adding an activator to a silicone acrylic hybrid composition to provide an activator-containing pressure sensitive adhesive mixture,
the silicone acrylic hybrid composition comprising:
a) a silicone acrylic hybrid pressure sensitive adhesive, and
b) a solvent, wherein the phase arrangement of the silicone phase and the acrylic phase in the initial silicone acrylic hybrid composition forming a continuous external phase and a discontinuous internal phase is determined by the solvent, wherein the activator
   a) is liquid at 20° C. and 1013 mbar,
   b) has a boiling point which is higher than the boiling point of the solvent and/or has a vapor pressure at 20° C. which is lower than the vapor pressure of the solvent contained in the silicone acrylic hybrid composition, and
   c) provides better dissolution properties for the inner phase of the initial silicone acrylic hybrid composition than the solvent contained in the silicone acrylic hybrid composition,
ii) coating said activator-containing pressure sensitive adhesive mixture on a film or release liner in an amount to provide the desired coating dry weight,
iii) drying said coated activator-containing pressure sensitive adhesive mixture to provide a pressure sensitive adhesive film or layer with the desired coating dry weight.

According to one aspect, the invention relates to a pressure sensitive adhesive film or layer prepared in accordance with the previous paragraph wherein the pressure sensitive adhesive film or layer has a continuous, silicone external phase and a discontinuous, acrylic internal phase or a continuous, acrylic external phase and a discontinuous, internal silicone phase.

According to a certain embodiment, the invention relates to a method of preparing a pressure sensitive adhesive film or layer having a continuous, silicone external phase and a discontinuous, acrylic internal phase based on a silicone acrylic hybrid composition which contains a continuous, acrylic external phase and a discontinuous, silicone internal phase, comprising the steps of:
i) adding an activator to a silicone acrylic hybrid composition to provide an activator-containing pressure sensitive adhesive mixture, wherein the activator is optionally mixed with an active agent and optionally further excipients and/or additives before added to the silicone acrylic hybrid composition,
   the silicone acrylic hybrid composition comprising:
      a) a silicone acrylic hybrid pressure sensitive adhesive, and
      b) ethyl acetate, wherein the phase arrangement of the silicone phase and the acrylic phase in the initial silicone acrylic hybrid composition forming a continuous, acrylic external phase and a discontinuous, silicon internal phase is determined by ethyl acetate,
   wherein preferably the activator is added in an amount of at least 10% of the total solvent volume contained in the silicone acrylic hybrid composition, and
   wherein the activator
      a) is liquid at 20° C. and 1013 mbar,
      b) has a boiling point which is higher than the boiling point of ethyl acetate and/or has a vapor pressure at 20° C. which is lower than the vapor pressure of ethyl acetate, and
      c) provides better dissolution properties for the inner phase of the initial silicone acrylic hybrid composition than ethyl acetate,
ii) coating said activator-containing pressure sensitive adhesive mixture on a film or release liner in an amount to provide the desired coating dry weight,
iii) drying said coated activator-containing pressure sensitive adhesive mixture to provide a pressure sensitive adhesive film or layer with the desired coating dry weight.

According to a certain embodiment, the invention relates to a method of preparing a pressure sensitive adhesive film or layer having a continuous, acrylic external phase and a discontinuous, silicone internal phase based on a silicone acrylic hybrid composition which contains a continuous, silicone external phase and a discontinuous, acrylic internal phase, comprising the steps of:
i) adding an activator to a silicone acrylic hybrid composition to provide an activator-containing pressure sensitive adhesive mixture, wherein the activator is optionally mixed with an active agent and optionally further excipients and/or additives before added to the silicone acrylic hybrid composition,
   the silicone acrylic hybrid composition comprising:
      a) a silicone acrylic hybrid pressure sensitive adhesive, and
      b) n-heptane, wherein the phase arrangement of the silicone phase and the acrylic phase in the initial silicone acrylic hybrid composition forming a continuous, silicone external phase and a discontinuous, acrylic internal phase is determined by n-heptane,
   wherein preferably the activator is added in an amount of at least 10% of the total solvent volume contained in the silicone acrylic hybrid composition, and
   wherein the activator
      a) is liquid at 20° C. and 1013 mbar,
      b) has a boiling point which is higher than the boiling point of n-heptane and/or has a vapor pressure at 20° C. which is lower than the vapor pressure of n-heptane, and
      c) provides better dissolution properties for the inner phase of the initial silicone acrylic hybrid composition than n-heptane,
ii) coating said activator-containing pressure sensitive adhesive mixture on a film or release liner in an amount to provide the desired coating dry weight,
iii) drying said coated activator-containing pressure sensitive adhesive mixture to provide a pressure sensitive adhesive film or layer with the desired coating dry weight.

According to one aspect, the invention relates to a transdermal drug delivery system comprising a pressure sensitive adhesive film or layer prepared by a method according to the previous paragraphs.

Within the meaning of this invention, the term "pressure sensitive adhesive" or "PSA" refers in particular to a material that adheres with finger or hand pressure, is permanently tacky, exerts a strong holding force and should be removable from smooth surface without leaving a residue. The pressure-sensitive adhesive properties of a polymer-based pressure-sensitive adhesive depend on the polymer or polymer mixture used. Examples of pressure sensitive adhesives are pressure sensitive adhesive polysiloxanes.

The terms "pressure sensitive adhesive composition" and "pressure sensitive adhesive mixture" refer to a pressure sensitive adhesive at least in mixture with a solvent (e.g. n-heptane or ethyl acetate). Examples of pressure sensitive adhesive compositions include the PSA series 7-4300 and 7-6300 manufactured and supplied in n-heptane or ethyl acetate by Dow Corning.

Within the meaning of this invention, the term "pressure sensitive adhesive film" refers to a pressure sensitive adhesive film or a pressure sensitive adhesive layer obtained from a solvent-containing adhesive coating mixture or composition after coating on a film and evaporating the solvents. The pressure sensitive adhesive film may also be referred to as pressure sensitive adhesive layer, in particular when it is used in a transdermal drug delivery system.

Within the meaning of this invention, the term "silicone acrylic hybrid" is intended to denote more than a simple blend of a silicone-based sub-species and an acrylate-based sub-species. Instead, the term denotes a polymerized hybrid species that includes silicone-based sub-species and acrylate-based sub-species that have been polymerized together. The "silicone acrylic hybrid pressure sensitive adhesive" thus comprises a silicone phase and the acrylic phase and may also be referred to as a "silicone acrylate hybrid pressure sensitive adhesive" as the terms acrylate and acrylic are generally used interchangeably in the context of the PSAs.

Within the meaning of this invention, the term "non-hybrid pressure sensitive adhesive (PSA)" is used synonymous for the pressure sensitive adhesives which do not include a hybrid species (e.g. for the silicone and acrylate PSAs).

Within the meaning of this invention, the term "silicone acrylic (SilAc) hybrid composition" corresponds to the terms "silicone acrylic (SilAc) hybrid pressure sensitive adhesive (PSA) composition" or "silicone acrylic (SilAc) hybrid pressure sensitive adhesive (PSA) mixture" and refers to a silicone acrylic hybrid pressure sensitive adhesive at least in mixture with a solvent (e.g. n-heptane or ethyl acetate). Examples of silicone acrylic hybrid compositions include the PSA series 7-6100 and 7-6300 manufactured and supplied in n-heptane or ethyl acetate by Dow Corning. A silicone acrylic hybrid composition according to the present invention may also include a non-hybrid PSA, for example a silicone-based PSA.

Within the meaning of this invention, the term "initial silicone acrylic hybrid composition" refers to the silicone acrylic hybrid composition before the activator is added.

Within the meaning of this invention, the term "phase arrangement" refers to the different orientation of the silicone phase and the acrylic phase in a silicone acrylic hybrid pressure sensitive adhesive composition. Depending on the solvent of the initial silicone acrylic hybrid composition the composition contains a continuous, silicone external phase and a discontinuous, acrylic internal phase (n-heptane) or a continuous, acrylic external phase and a discontinuous, silicone internal phase (ethyl acetate). The phase arrangement of the compositions can, for example, be determined in peel force tests with pressure sensitive adhesive films prepared from the SilAc hybrid PSA compositions which are attached to a siliconized release liner. The pressure sensitive adhesive film contains a continuous, silicone external phase if the siliconized release liner cannot or can only hardly be removed from the pressure sensitive adhesive film (laminated to a backing film) due to the blocking of the two silicone surfaces. Blocking results from the adherence of two silicone layers which comprise a similar surface energy. The silicone adhesive shows a good spreading on the siliconized liner and therefore can create a good adhesion to the liner. If the siliconized release liner can easily be removed the pressure sensitive adhesive film contains a continuous, acrylic external phase. The acrylic adhesive has no good spreading due to the different surface energies and thus has a low or almost no adhesion to the siliconized liner.

Within the meaning of this invention, the term "activator" refers to a substance that induces an inversion of the phase arrangement in a silicone acrylic hybrid pressure sensitive adhesive composition containing a continuous external phase and a discontinuous internal phase. The activator is liquid at 20° C. and 1013 mbar and has a boiling point which is higher than the boiling point of the solvent or has a vapor pressure at 20° C. which is lower than the vapor pressure of the solvent, and provides better dissolution properties for the inner phase of the initial silicone acrylic hybrid composition than the solvent contained in the silicone acrylic hybrid composition. Better dissolution properties for the inner phase are achieved when the inner phase has a higher solubility in the activator than in the solvent. In several cases the activator has a boiling point which is higher than the boiling point of the solvent and additionally has a vapor pressure at 20° C. which is lower than the vapor pressure of the solvent.

Within the meaning of this invention, the term "volatile silicone" refers to low molecular weight low viscosity silicone oils and fluids. The term "silicone fluid" refers to liquid low viscosity (0.5 cSt up to 5.0 cSt) siloxanes such as hexamethyldisiloxane, octamethyltrisiloxane, or decamethyltetrasiloxane. Silicone fluids which are commercially available include Silicone fluid 0.65 cSt, Silicone fluid 1.0 cSt, Silicone fluid 1.5 cSt. They are characterized by low molecular weights, low surface tension, volatility, high compressibility and excellent low temperature performance.

Within the meaning of this invention, the term "area weight" and "coating dry weight" are used interchangeably and refer to the dry weight of an individual film or layer, except backing layer or release liner, and is provided in $g/m^2$. Amounts of active agent or polymer in a layer provided in $mg/cm^2$ or % refer to or are based on the area weight of the layer.

Within the meaning of this invention, the term "transdermal drug delivery system" (or TDDS) refers to the entire individual unit that is applied to the skin of a patient, and which comprises the pressure sensitive adhesive film or layer comprising an active agent, a backing layer and optionally further active agent-containing layers or active agent-free layers or an additional larger active-free self-adhesive layer structure, which TDDS provides the percutaneous delivery of the active agent to the patient. During storage, such a TDDS is normally located on a re-detachable protective layer or release liner from which it is removed immediately before application to the surface of the patient's skin. A TDDS protected this way may be stored in sealed pouches. The layer structure of a TDDS includes at least a backing layer, an adhesive layer. The layer structure may comprise, for example, a backing layer, a pressure sensitive adhesive layer comprising an active agent and optionally an additional skin contact layer.

DETAILED DESCRIPTION

Pressure Sensitive Adhesive Compositions

The silicone acrylic hybrid composition used in the present invention comprises a silicone acrylic hybrid pressure sensitive adhesive (PSA) and at least a solvent. The pressure sensitive adhesive compositions are supplied and used in solvents like n-heptane and ethyl acetate. The solids content of the pressure sensitive adhesive compositions is usually between 40% and 80%. Examples of silicone acrylic hybrid PSA compositions include the PSA series 7-6100 and 7-6300 manufactured and supplied in n-heptane or ethyl acetate by Dow Corning (7-630X (X=1 n-heptane-based/ X=2 ethyl acetate-based).

The arrangement of the silicone phase and the acrylic phase depends on the solvent in which the SilAc hybrid PSA is supplied. If the SilAc hybrid PSA composition is heptane-based, the composition contains a continuous, silicone external phase and a discontinuous, acrylic internal phase. If the SilAc hybrid PSA composition is ethyl acetate-based, the composition contains a continuous, acrylic external phase and a discontinuous, silicone internal phase.

The silicone acrylic hybrid composition according to the present invention may further comprise a non-hybrid pressure sensitive adhesive, e.g. a pressure sensitive adhesive based on polysiloxanes or acrylates.

The silicone acrylic hybrid pressure sensitive adhesive comprises the reaction product of silicon-containing pressure sensitive adhesive composition comprising acrylate or methacrylate functionality, an ethylenically unsaturated monomer, and an initiator. That is, the silicone acrylic hybrid PSA is the product of the chemical reaction between these reactants (the silicone-containing pressure sensitive adhesive composition, the ethylenically unsaturated monomer, and the initiator). In particular, the silicone acrylic hybrid pressure sensitive adhesive includes the reaction product of a silicone-containing pressure sensitive adhesive composition comprising acrylate or methacrylate functionality, a (meth)acrylate monomer, and an initiator (i.e., in the presence of the initiator). That is, the silicone acrylic hybrid PSA includes the product of the chemical reaction between these reactants (the silicone-containing pressure sensitive adhesive composition, the (meth)acrylate monomer, and the initiator). The silicone-containing pressure sensitive adhesive composition is typically present in the hybrid pressure sensitive adhesive in an amount of from 5 to 95, more typically 25 to 75, parts by weight based on 100 parts by weight of the hybrid pressure sensitive adhesive.

The silicone acrylic hybrid composition used in the present invention may be described by being prepared by a method comprising the steps of:
(i) providing a silicon-containing pressure sensitive adhesive composition comprising acrylate or methacrylate functionality and the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE- where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to total a pressure sensitive adhesive, wherein the silicon-containing capping agent is introduced prior to, during, or after the silicone resin and silicone polymer are reacted, and wherein:
    the silicon-containing capping agent reacts with the pressure sensitive adhesive after the silicone resin and silicone polymer have been condensation reacted to form the pressure sensitive adhesive; or
    the silicon-containing capping agent reacts in-situ with the silicone resin and silicone polymer;
(ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
(iii) removing the first solvent; and
(iv) adding a second solvent to form the silicone acrylic hybrid composition, wherein the phase arrangement of the silicone acrylic hybrid composition is selectively controlled by selection of the second solvent.

The silicone acrylic hybrid PSA composition used in the present invention may also be described by being prepared by a method comprising the steps of:
(i) providing a silicon-containing pressure sensitive adhesive composition comprising acrylate or methacrylate functionality and the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE- where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to form a pressure sensitive adhesive, wherein the silicon-containing capping agent is introduced prior to, during, or after the silicone resin and silicone polymer are reacted, and wherein:
    the silicon-containing capping agent reacts with the pressure sensitive adhesive after the silicone resin and silicone polymer have been condensation reacted to form the pressure sensitive adhesive; or
    the silicon-containing capping agent reacts in-situ with the silicone resin and silicone polymer;
(ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
(iii) adding a processing solvent, wherein the processing solvent has a higher boiling point than the first solvent, and
(iv) applying heat at a temperature of from 70° C. to 150° C. such that a majority of the first solvent is selectively removed;
(v) removing the processing solvent; and.
(vi) adding a second solvent to form the silicone acrylic hybrid composition, wherein the phase arrangement of the silicone acrylic hybrid composition is selectively controlled by selection of the second solvent.

The ethylenically unsaturated monomer may be a compound selected from the group of aliphatic acrylates, aliphatic methacrylates, cycloaliphatic acrylates, cycloaliphatic methacrylates, and combinations thereof, each of said compounds having up to 20 carbon atoms in the alkyl radical, wherein said aliphatic acrylates are optionally selected from the group of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and combinations thereof,
and said aliphatic methacrylates are selected from the group of methyl methacrylate, ethyl methacrylate, propyl methacrylate, n-butyl methacrylate, iso-butyl methacrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, and combinations thereof.

The non-hybrid pressure sensitive adhesive compositions used in the present invention are polymer-based pressure sensitive adhesive compositions. The pressure sensitive adhesive compositions are supplied and used in solvents like n-heptane and ethyl acetate. The solids content of the pressure sensitive adhesive compositions is usually between 30% and 80%. In particular, silicone-containing pressure sensitive adhesives may have a solids content between 60% and 80%, acrylate-containing pressure sensitive adhesives may have a solids content between 30% and 60%.

Silicone-containing pressure sensitive adhesives may also be referred to as silicone-based pressure sensitive adhesives, silicone pressure sensitive adhesives or pressure sensitive adhesives based on polysiloxanes. Such silicone-based PSAs need, unlike other organic pressures sensitive adhesives, no additives like antioxidants, stabilizers, plasticizers, catalysts or other potentially extractable ingredients. These pressure sensitive adhesives provide for suitable tack for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure sensitive adhesives are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The dimethiconol content contributes to the viscous component of the viscoelastic behavior, and impacts the wetting and the spreadability properties of the adhesive. The resin acts as a tackifying and reinforcing agent, and participates in the elastic component. The correct balance between dimethiconol and resin provides for the correct adhesive properties.

Examples of silicone based PSA compositions which are commercially available include the standard BIO-PSA series (7-4400, 7-4500 and 7-4600 series), the amine compatible (endcapped) BIO-PSA series (7-4100, 7-4200 and 7-4300 series) and the Soft Skin Adhesives series (7-9800) manufactured and typically supplied in n-heptane or ethyl acetate by Dow Corning. For example, BIO-PSA 7-4201 is characterized by a solution viscosity at 25° C. and about 60% solids content in heptane of 450 mPa s and a complex viscosity at 0.01 rad/s at 30° C. of $1\times10^8$ Poise. BIO-PSA 7-4301 has a solution viscosity at 25° C. and about 60% solids content in heptane of 500 mPa s and a complex viscosity at 0.01 rad/s at 30° C. of $5\times10^6$ Poise.

Acrylate-containing pressure-sensitive adhesives may also be referred to as acrylate-based pressure sensitive adhesives, acrylate pressure sensitive adhesives or pressure sensitive adhesives based on acrylates. Such acrylate-based pressure sensitive adhesives are, for example, pressure sensitive adhesives based on an acrylate-vinylacetate polymer, e.g., such as those available from Henkel under the tradename Duro Tak®, e.g., Duro Tak® 387 2051. Such pressure-sensitive adhesives are provided in ethyl acetate and heptane. Such pressure-sensitive adhesives provide a 180° Peel at 20 minutes of at least about 20 N/25 mm, and at 24 minutes of at least about 25 N/25 cm, and at one week of at least about 30 N/25 mm and a Loop tack of at least 15 N/25 mm$^2$, or of at least 20 N/25 mm$^2$, or of at least 22 N/25 mm$^2$.

Activator

The activator used in the present invention is a substance that induces an inversion of the phase arrangement in a silicone acrylic hybrid pressure sensitive adhesive composition containing a continuous external phase and a discontinuous internal phase. The activator is liquid at 20° C. and 1013 mbar, has a boiling point which is higher than the boiling point of the solvent and/or has a vapor pressure at 20° C. which is lower than the vapor pressure of the solvent of the silicone acrylic hybrid composition, and provides better dissolution properties for the inner phase of the initial silicone acrylic hybrid composition than the solvent contained in the silicone acrylic hybrid composition. According to certain embodiments of the invention the activator is the activator is liquid at 20° C. and 1013 mbar, has a boiling point which is higher than the boiling point of the solvent and has a vapor pressure at 20° C. which is lower than the vapor pressure of the solvent of the silicone acrylic hybrid composition, and provides better dissolution properties for the inner phase of the initial silicone acrylic hybrid composition than the solvent contained in the silicone acrylic hybrid composition.

The activator may be selected, for example, from a volatile silicone (e.g. silicone fluids such as silicone fluid 1.0 cSt), an aliphatic solvent (e.g. n-heptane, n-octane), an aromatic solvent, a ketone, an aldehyde, an alcohol (e.g. glycols), an ester (e.g. propyl acetate, butyl acetate), a halogenated solvent, a mineral spirit, and combinations thereof.

According to a certain embodiment of the invention, wherein the solvent of the silicone acrylic hybrid composition is ethyl acetate, the activator has a boiling point which is higher than the boiling point of ethyl acetate and/or has a vapor pressure at 20° C. which is lower than the vapor pressure of ethyl acetate.

For example, in case the silicone acrylic hybrid composition includes ethyl acetate as the solvent, the silicone acrylic hybrid composition contains a continuous, acrylic external phase and a discontinuous, silicone internal phase. Ethyl acetate has a boiling point of about 77° C. and a vapor pressure of about 98 hPa (20° C.). Suitable activators for a phase inversion are liquid substances with a boiling of more than 77° C. and/or a vapor pressure of less than 98 hPa (20° C.) and which provide better dissolution properties for the silicone phase than the solvent ethyl acetate provide. For example, a hydrophobic compound like n-heptane with a boiling point of about 98° C. and a vapor pressure of about 47 hPa (20° C.) is a suitable activator for a phase inversion since the silicone phase has a better solubility in n-heptane than in the solvent ethyl acetate.

According to a certain embodiment of the invention, wherein the initial silicone acrylic hybrid composition contains a continuous, acrylic external phase and a discontinuous, silicone internal phase, the activator is selected from a volatile silicone, an aliphatic hydrocarbon, and combinations thereof.

According to a certain embodiment of the invention, wherein the initial silicone acrylic hybrid composition contains a continuous, acrylic external phase and a discontinuous, silicone internal phase, the activator is selected from silicone fluid, an aliphatic hydrocarbon, and combinations thereof.

According to a certain embodiment of the invention, wherein the initial silicone acrylic hybrid composition contains a continuous, acrylic external phase and a discontinuous, silicone internal phase, the activator is selected from hexamethyldisiloxane, octamethyltrisiloxane, decamethyltetrasiloxane, n-heptane, n-octane, and combinations thereof.

According to a certain embodiment of the invention, wherein the solvent of the silicone acrylic hybrid composition is n-heptane, the activator has a boiling point which is higher than the boiling point of n-heptane and/or has a vapor pressure at 20° C. which is lower than the vapor pressure of n-heptane.

For example, in case the silicone acrylic hybrid composition includes n-heptane as the solvent, suitable activators are liquid substances with a boiling of more than 98° C. and/or a vapor pressure of less than 47 hPa (20° C.) and which provide a better solubility for the acrylic phase than the solvent n-heptane. Such activators include but are not limited to acetates such as propyl acetate and butyl acetate.

According to a certain embodiment of the invention, wherein the initial silicone acrylic hybrid composition contains a continuous, silicone external phase and a discontinuous, acrylic internal phase, the activator is selected from an ester (e.g. an acetate), an alcohol (e.g. a glycol), and combinations thereof.

According to a certain embodiment of the invention, wherein the initial silicone acrylic hybrid composition contains a continuous, silicone external phase and a discontinuous, acrylic internal phase, the activator is selected from propyl acetate, butyl acetate, ethylene glycol, propylene glycol, and combinations thereof.

The activator can be added in any amount but is preferably added in an amount of at least 10%, at least 15%, or at least 20% of the total solvent volume contained in the silicone acrylic hybrid composition. The activator can be added in an amount of from about 10% to 100%, or from about 15% to 100%, or from about 20% to 100%, or from about 10% to about 80%, or from about 15% to about 80%, or from about 20% to about 80%, or from about 10% to 75%, or from about 15% to 75%, or from about 20% to 75%, or from about 30% to about 75%, or from about 40% to about 75%, or from about 10% to about 50%, or from about 15% to about 50%, or from about 20% to about 50%, or from about 10% to about 45%, or from about 15% to about 45%, or from about 20% to about 45% of the silicone acrylic hybrid composition of the total solvent volume contained in the silicone acrylic hybrid composition.

According to a certain embodiment of the invention, wherein the silicone acrylic hybrid composition contains a continuous, acrylic external phase and a discontinuous, silicone internal phase, the solvent of the silicone acrylic hybrid composition is ethyl acetate, the activator is n-heptane or silicone fluid and is added in an amount of at least 10%, at least 15%, or at least 20% of the total solvent volume contained in the silicone acrylic hybrid composition.

According to a certain embodiment of the invention, wherein the initial silicone acrylic hybrid composition contains a continuous, silicone external phase and a discontinuous, acrylic internal phase, the solvent of the silicone acrylic hybrid composition is n-heptane, the activator is propyl acetate or butyl acetate and is added in an amount of at least 10%, at least 15%, or at least 20% of the total solvent volume contained in the silicone acrylic hybrid composition.

Pressure Sensitive Adhesive Film

The pressure sensitive adhesive film prepared according to the invention may also be referred to as pressure sensitive adhesive layer, in particular when it is used in a transdermal delivery system.

The method of preparing a pressure sensitive adhesive film or layer comprises the steps of:
i) adding an activator (e.g. n-heptane, or silicone fluid 1.0 cSt) to a silicone acrylic hybrid composition to provide an activator-containing pressure sensitive adhesive mixture,
ii) coating said activator-containing pressure sensitive adhesive mixture on a film or release liner in an amount to provide the desired coating dry weight,
iii) drying said coated activator-containing pressure sensitive adhesive mixture to provide a pressure sensitive adhesive film or layer with the desired coating dry weight.

According to certain embodiments of the invention, the activator is mixed with an active agent and optionally further excipients and/or additives before added to the silicone acrylic hybrid composition.

According to certain embodiments of the invention, the active agent is insoluble or has a limited solubility at 20° C. in the silicone acrylic hybrid composition.

According to certain embodiments of the invention, the active agent is insoluble or has a limited solubility at 20° C. in the activator.

According to a certain embodiment of the invention, the active agent is insoluble or has a limited solubility at 20° C. in the silicone acrylic hybrid composition and in the activator.

The pressure sensitive adhesive film or layer prepared according to the invention may thus comprise an active agent (e.g. felodipine, IUPAC name: (RS)-3-ethyl 5-methyl 4-(2,3-dichlorophenyl)-2,6-dimethyl-1,4-dihydropyridine-3,5-dicarboxylate) and other various excipients or additives, for example from the group of solubilizers, fillers, tackifiers, enhancers (substances which influence the barrier properties of the stratum corneum in the sense of increasing the active agent permeability), pH regulators, and preservatives.

The pressure sensitive adhesive film or layer may contain the active agent in a therapeutically effective amount, e.g., in an amount of from about 1 to about 20 weight-% of the pressure sensitive adhesive film or layer. According to a certain embodiment, the active agent (e.g. felodipine) is present in an amount of about 2 to 10 weight-% of the pressure sensitive adhesive film or layer.

According to certain embodiments of the invention, the activator-containing pressure sensitive adhesive mixture can be homogenized before coating, e.g., for 5 min at 2000 rpm, followed by 10 min at 1000 rpm. For the homogenizing step, a propeller stirrer and an overhead stirrer RW 20 can be used.

The activator-containing pressure sensitive adhesive mixture can be coated using a film applicator from the company Erichsen according to the solids content of the mixture under consideration of the desired coating dry weight, for example, with a gap of 300-400 μm, with speed transport roll of 1.5 m/min and a speed doctor roll of 0.2 m/min.

The pressure sensitive adhesive film or layer may be coated at any coating dry weight but is preferably coated at a coating dry weight of about 30 $g/m^2$ to about 400 $g/m^2$, or of about 30 $g/m^2$ to about 200 $g/m^2$, or of about 100 $g/m^2$ to about 200 $g/m^2$. According to a certain embodiment, the pressure sensitive adhesive film or layer is coated at a coating dry weight of about 50 $g/m^2$ to about 120 $g/m^2$.

The film or release liner can be any of the typical materials used for tapes and films depending on its function in the final product and the phase arrangement of the silicone phase and acrylic phase in the coating mixture.

The material of the release liner can, for example, be dependent upon the phase arrangement in the coating mixture. For a hybrid composition that contains an external acrylic phase, for example, a silicone-based release liner (e.g. Dow Corning® Syl-off™ 7680) can be used. For a hybrid composition that contains an external silicone phase then, for example, either a fluoropolymer coated polyester liner (e.g. 3M Scotchpak 9755), perfluoropolyether-based release liners (e.g. 3M SCOTCH-PAK® 1022 Release Liner) or fluorosilicone-based release liners (e.g. Dow Corning® Syl-off™ 02-7785) can be chosen.

According to certain embodiments of the invention the activator-containing pressure sensitive adhesive mixture is coated on a fluoropolymer coated polyester release liner (3M Scotchpak 9755).

The activator-containing pressure sensitive adhesive mixture can also be coated on a film which is not used as a release liner, e.g., the film can have the function of a backing layer of the pressure sensitive adhesive film or layer. Suitable film materials are, for example, those selected from polymeric films (e.g. polyethylene, polyester, polyimide, polyolefins, polypropylene, polyurethane, PTFE, etc.), metal foils, glass cloth, PTFE-coated glass cloth, paper (e.g. crepe, super-calendared craft, etc.), cloth, nonwoven materials, foams (e.g. polyurethane, acrylate, silicone, neoprene, etc.) and rubbers (e.g. silicone, butyl, etc.).

The coated activator-containing pressure sensitive adhesive mixture can be dried in a heating and drying oven, for example at 50° C. for 10 min.

Without wishing to be bound to any theory it is believed that during the drying step, the activator is removed later than the solvent of the silicone acrylic hybrid composition and promotes the phase which has a higher solubility in the activator to be arranged as the continuous external phase.

The pressure sensitive adhesive film or layer may further comprise a non-hybrid pressure sensitive adhesive, e.g. a silicone-based pressure sensitive adhesive or an acrylate-based pressure sensitive adhesive. The pressure sensitive adhesive film or layer further comprises a non-hybrid pressure sensitive adhesive, for example, when the pressure sensitive adhesive film or layer is prepared from a silicone acrylic hybrid composition comprising a composition selected from the hybrid PSA series 7-6300 (e.g. 7-6302) and a composition selected from the non-hybrid PSA series 7-4300 (e.g. 7-4301) manufactured and supplied by Dow Corning.

The pressure sensitive adhesive film or layer can also be laminated to a backing layer (e.g. a PET film) and/or to further polymer films or layers, for example, when the pressure sensitive adhesive film or layer is used for the preparation of a transdermal drug delivery system. A transdermal drug delivery system may also consist of an active agent-containing pressure sensitive adhesive film which is laminated to a backing layer and punched to the desired area of release. The backing layer can be any of the typical substrates used for tapes such as those selected from polymeric films (e.g. polyethylene, polyester, polyimide, polyolefins, polypropylene, polyurethane, PTFE, etc.), metal foils, glass cloth, PTFE-coated glass cloth, paper (e.g. crepe, super-calendared craft, etc.), cloth, nonwoven materials, foams (e.g. polyurethane, acrylate, silicone, neoprene, etc.) and rubbers (e.g. silicone, butyl, etc.).

Peel Force Test

The phase arrangement of the compositions can be determined by a peel force test with a tensile strength testing machine (Instron Model 1122) with pressure sensitive adhesive films prepared from the SilAc hybrid PSA compositions. For this purpose, the pressure sensitive adhesive films were laminated with a transparent PET film as backing film and transferred from the Scotchpak release liner to a siliconized PET release liner, in particular the siliconized side.

Sample testing with the tensile strength testing machine:

The T carrier is gripped inserted into the lower clamp jaw of the tensile strength testing machine. The bearing surface is fitted with double-sided adhesive tape. The rear side of the protective liner (i.e., the unsiliconized side of the siliconized release liner) is sticked to the splicing tape. The sample is fixed carefully to the double sided adhesive tape with the adhesive surface face down by gentle stroking manually longitudinal direction. The free end of the splicing tape is attached to the upper jaw and is peeled off without delay. The distance between upper and lower clamp should be at least 250 mm in order to avoid any deviation from pull off angle of 90°. The pull-off speed is 150 mm/min.

If the pressure sensitive adhesive film contains a continuous, silicone external phase the transfer to the siliconized release liner causes a blocking of the surfaces and the siliconized release liner cannot or can only hardly be removed from the sample (the pressure sensitive adhesive film laminated to a backing film). In such cases the test result of the sensoric testing is "yes" (blocked). The sensoric blocking degree can further be determined by "+" (blocking but the liner can still be separated from the film with some force without damaging the film of the liner) up to "+++" (highest blocking degree up to completely blocked).

If the pressure sensitive adhesive film contains a continuous, acrylic external phase the siliconized release liner can easily be removed from the sample. In such cases the test result of the sensoric testing is "no" (no blocking).

EXAMPLES

The present invention will now be more fully described with reference to the accompanying examples. It should be understood, however, that the following description is illustrative only and should not be taken in any way as a restriction of the invention.

Example 1

The compositions of the pressure sensitive adhesive films and the results of the peel force test are summarized in Table 1 below.

TABLE 1

| Sample | Felodipine [%] | Adhesive [%] | Solvent in the coating mixture [Parts] | | Activator in the coating mixture [Parts] | Area weight [g/m$^2$] | Sensoric testing - Peel behavior (blocking degree) [yes/no] |
|---|---|---|---|---|---|---|---|
| A1 | 6 | SilAc 7-630194 | n-Hept 100 | | — | 81 | yes +++ |
| B1 | 6 | SilAc 7-630194 | MEK 19 | n-Hept 91 | — | 80 | yes +++ |

TABLE 1-continued

| Sample | Felodipine [%] | Adhesive [%] | | Solvent in the coating mixture [Parts] | Activator in the coating mixture [Parts] | Area weight [g/m²] | Sensoric testing - Peel behavior (blocking degree) [yes/no] |
|---|---|---|---|---|---|---|---|
| C1 | 6 | SilAc 7-630294 | | Etac 100 | — | 104 | no |
| 1 | 6 | SilAc 7-630294 | | Etac 40 | n-Oct 60 | 105 | yes +++ |
| 2 | 6 | SilAc 7-630294 | | Etac 40 | SilF 1cSt 60 | 85 | yes +++ |
| 3 | 3.6 | SilAc 7-630257.84 | BIO-PSA 7-430138.56 | Etac 77 | n-Hept 23 | 104 | yes +++ | n-Hept = n-heptane,
n-Oct = n-octane,
Etac = ethyl acetate,
MEK = methyl ethyl ketone,
SilF = Silicone fluid 1.0 cSt Preparation of the Active Agent-Containing Pressure Sensitive Adhesive Films:

The amount of active agent (felodipine) is mixed with parts of the solvent of the chosen SilAc hybrid composition SilAc 7-630X (X=1 n-heptane-based/X=2 ethyl acetate-based) (samples A1, C1, and 1-3) or with an added solvent (MEK, sample B1 and optionally further excipients or enhancers, and, in case of the inventive examples 1-3, additionally with the activator (Silicone fluid 1.0 cSt, n-octane, or n-heptane). This mixture is sonicated for 5 min and subsequently added to the SilAc hybrid composition. In sample 3, the SilAc hybrid composition is additional mixed with a non-hybrid amine-compatible silicone pressure sensitive adhesive composition including heptane (BIO-PSA 7-4301). The exact adhesive quantity depends on the used amount of all compounds, but all components sum up in total to 100%.

The resulting pressure sensitive adhesive mixture is homogenized for further 5 min at 2000 rpm using a propeller stirrer and an IKA overhead stirrer RW 20. For the next 10 min the stirring speed was reduced to 1000 rpm. The homogenized active agent-containing pressure sensitive adhesive mixture is coated onto a release liner, for example 3M Scotchpak 9755, with a film applicator from the company Erichsen (according to the solids content of the pressure sensitive adhesive mixture, e.g. with a gap of 300-400 µm, speed transport roll of 1.5 m/min and speed doctor roll of 0.2 m/min) under consideration of the desired coating weight. The coated pressure sensitive adhesive mixture was dried in a heating and drying oven at 50° C. for 10 min to provide a pressure sensitive adhesive film.

Peel Force Tests:

For the peel force tests the pressure sensitive adhesive films were laminated with a transparent PET film as backing film and transferred from the Scotchpak release liner to a siliconized PET release liner, in particular the siliconized side. The samples were stored at room temperature under nitrogen in sealed pouches until used. The sealing temperature of the pouches was 180° C.

The results of the peel force test show that the phase arrangement of the inventive samples prepared with an ethyl acetate-based SilAc hybrid composition and an activator (samples 1-3) is inverted compared to the pressure sensitive adhesive film prepared with an ethyl acetate-based SilAc hybrid composition and without an activator (sample C). The phase arrangement of the inventive samples 1-3 corresponds to the phase arrangement of samples A1 and B1 prepared with a heptane-based SilAc hybrid composition.

Example 2

The compositions of the pressure sensitive adhesive films are summarized in Table 2 below.

TABLE 2

| | Sample | | | |
|---|---|---|---|---|
| | A2 | B2 | C2 | 4 |
| Excipients | Composition [%] | | | |
| Felodipine | 4.00 | 4.00 | 4.00 | 4.00 |
| SilAc 7-6301 (n-Heptan based) | 96.00 | 96.00 | n.a. | n.a. |
| n-Heptan | adjustment of solids content | adjustment of solids content | n.a. | n.a. |
| Methyl ethyl ketone | n.a. | dissolution of active agent | n.a. | n.a. |
| SilAc 7-6302 (Ethyl acetate based) | n.a. | n.a. | 96.00 | 96.00 |
| Ethyl acetate | n.a. | n.a. | adjustment of solids content | adjustment of solids content |

TABLE 2-continued

| Excipients | A2 | B2 | C2 | 4 |
|---|---|---|---|---|
| | | Sample Composition [%] | | |
| Silicone fuid 1 cSt | n.a. | n.a. | n.a. | activator for phase inversion |
| Total | 100 | 100 | 100 | 100 |
| Solids content [%] adhesive mass | 50 | 50 | 50 | 50 |
| Area weight [g/m$^2$] | 108 | 105 | 93 | 78 |
| Ratio of solvents/ solvent and activator | n-Heptan 100 | n-Heptan MEK 91:9 | Etac 100 | Etac/SilF 40:60 |
| dissolution status of active agent | undissolved/ suspension of active agent in dried matrix | dissolved/re- crystallization in film | dissolved/film free of crystals | dissolved/film free of crystals |

Etac = ethyl acetate,
SilF—Silicone fluid 1.0 cSt

The pressure sensitive adhesive films A2, B2, C2 and 4 are prepared in accordance with the method of preparation described for the pressure sensitive adhesive films A1, B1, C1 and 1-3 in Example 1.

The preparation of a pressure sensitive adhesive film with a continuous, silicone external phase and a discontinuous, acrylic internal phase the heptane-based SilAc hybrid composition SilAc 7-6301 is used which leads to a film wherein the active agent felodipine is not dissolved but dispersed in the dried matrix (sample A2). For a satisfactory active agent permeation and utilization, however, it is necessary to provide a corresponding film wherein the active agent is dissolved in the dried adhesive matrix. The addition of a solvent (methyl ethyl ketone) for the active agent during the preparation process of the film initially results in a film wherein the active agent is dissolved, however, the film is not stable and after several weeks at room temperature the active agent recrystallizes in the adhesive matrix (sample B2). The preparation of a pressure sensitive adhesive film using the ethyl acetate-based SilAc hybrid composition SilAc 7-6302 results in a stable product wherein the active agent is dissolved, however, the pressure sensitive adhesive film has a continuous, acrylic external phase (sample C2).

In the preparation of inventive sample 4 Silicone fluid 1.0 cSt is added as an activator to the SilAc hybrid composition SilAc 7-6302. The addition of the activator leads to a phase inversion and the provision of a stable pressure sensitive adhesive film with a continuous, silicone external phase.

Example 3

The compositions of the pressure sensitive adhesive films and the results of the peel force test are summarized in Table 3 below.

TABLE 3

| Sample | Adhesive [%] | | Solvent in the coating mixture [Parts] | Activator in the coating mixture [Parts] | Area weight [g/m$^2$] | Sensoric testing - Peel behavior (blocking degree) [yes/no] |
|---|---|---|---|---|---|---|
| A3 | SilAc 7-6301 | 100 | n-Heptane 100 | | 45 | yes completely blocked |
| C3 | SilAc 7-6302 | 100 | Ethyl acetate 100 | | 71 | no |
| 5 | SilAc 7-6302 | BIO-PSA 7-4301 10 | Ethyl acetate 96 | n-Heptane 4 | 61 | no |
| 6 | SilAc 7-6302 | BIO-PSA 7-4301 20 | Ethyl acetate 91 | n-Heptane 9 | 62 | no |
| 7 | SilAc 7-6302 | BIO-PSA 7-4301 30 | Ethyl acetate 86 | n-Heptane 14 | 66 | yes completely blocked |
| 8 | SilAc 7-6302 | BIO-PSA 7-4301 40 | Ethyl acetate 79 | n-Heptane 21 | 65 | yes completely blocked |
| 9 | SilAc 7-6302 | BIO-PSA 7-4301 50 | Ethyl acetate 72 | n-Heptane 28 | 68 | yes completely blocked |
| 10 | SilAc 7-6302 | BIO-PSA 7-4301 60 | Ethyl acetate 63 | n-Heptane 37 | 69 | yes completely blocked |
| 11 | SilAc 7-6302 | BIO-PSA 7-4301 80 | Ethyl acetate 39 | n-Heptane 61 | 75 | yes completely blocked |

The active-agent free pressure sensitive adhesive films in Example 3 are prepared by coating the SilAc hybrid composition (SilAc 7-6301 or SilAc 7-6302) or the adhesive mixture onto a release liner, for example 3M Scotchpak 9755, with a film applicator from the company Erichsen (according to the solids content of the adhesive mixture, e.g. with a gap of 300-400 μm, speed transport roll of 1.5 m/min and speed doctor roll of 0.2 m/min) under consideration of the desired coating weight. The coated adhesive mixture was dried in a heating and drying oven at 50° C. for 10 min to provide a pressure sensitive adhesive film. For samples 5-11 the non-hybrid amine-compatible silicone PSA including heptane (BIO-PSA 7-4301) is admixed to the silicone acrylic hybrid composition (SilAc 7-6302) before coating.

The pressure sensitive adhesive films are prepared for peel force tests according to Example 1.

The results of the peel force test show that the phase arrangement of the inventive samples prepared with an ethyl acetate-based SilAc hybrid composition including additionally a non-hybrid silicone PSA can be inverted with the activator n-heptane. The phase arrangement of the inventive samples corresponds to the phase arrangement of sample A3 with a heptane-based SilAc hybrid composition.

The invention relates in particular to the following further items:

1. A method of inverting the phase arrangement of the silicone phase and the acrylic phase in a silicone acrylic hybrid composition,
the silicone acrylic hybrid composition comprising:
   a) a silicone acrylic hybrid pressure sensitive adhesive, and
   b) a solvent, wherein the phase arrangement of the silicone phase and the acrylic phase in the initial silicone acrylic hybrid composition forming a continuous external phase and a discontinuous internal phase is determined by the solvent,
comprising the step of adding an activator to the silicone acrylic hybrid composition, wherein the activator
   a) is liquid at 20° C. and 1013 mbar,
   b) has a boiling point which is higher than the boiling point of the solvent and/or has a vapor pressure at 20° C. which is lower than the vapor pressure of the solvent contained in the silicone acrylic hybrid composition, and
   c) provides better dissolution properties for the inner phase of the initial silicone acrylic hybrid composition than the solvent contained in the silicone acrylic hybrid composition.

2. A method of preparing a pressure sensitive adhesive film or layer based on a silicone acrylic hybrid composition comprising the steps of:
   i) adding an activator to a silicone acrylic hybrid composition to provide an activator-containing pressure sensitive adhesive mixture,
   the silicone acrylic hybrid composition comprising:
      a) a silicone acrylic hybrid pressure sensitive adhesive, and
      b) a solvent, wherein the phase arrangement of the silicone phase and the acrylic phase in the initial silicone acrylic hybrid composition forming a continuous external phase and a discontinuous internal phase is determined by the solvent,
   wherein the activator
      a) is liquid at 20° C. and 1013 mbar,
      b) has a boiling point which is higher than the boiling point of the solvent and/or has a vapor pressure at 20° C. which is lower than the vapor pressure of the solvent contained in the silicone acrylic hybrid composition, and
      c) provides better dissolution properties for the inner phase of the initial silicone acrylic hybrid composition than the solvent contained in the silicone acrylic hybrid composition,
   ii) coating said activator-containing pressure sensitive adhesive mixture on a film or release liner in an amount to provide the desired coating dry weight,
   iii) drying said coated activator-containing pressure sensitive adhesive mixture to provide a pressure sensitive adhesive film or layer with the desired coating dry weight.

3. The method according to item 2, wherein in step i) the activator is mixed with an active agent before added to the silicone acrylic hybrid composition.

4. The method according to item 2 or 3, wherein in step i) the activator is mixed with further excipients and/or additives before added to the silicone acrylic hybrid composition.

5. The method according to any one of items 2 to 4, wherein the active agent is insoluble or has a limited solubility at 20° C. in the silicone acrylic hybrid composition.

6. The method according to any one of items 2 to 5, wherein the active agent is insoluble or has a limited solubility at 20° C. in the activator.

7. The method according to any one of items 2 to 6, wherein the active agent is felodipine.

8. The method according to any one of items 1 to 7, wherein the silicone acrylic hybrid composition further comprises a non-hybrid pressure sensitive adhesive based on polysiloxanes or acrylates.

9. The method according to any one of items 1 to 8, wherein the silicone acrylic hybrid composition further comprises a non-hybrid pressure sensitive adhesive based on polysiloxanes.

10. The method according to any one of items 1 to 9, wherein the activator is added in an amount of at least 10%, at least 15%, or at least 20% of the total solvent volume contained in the silicone acrylic hybrid composition.

11. The method according to any one of items 1 to 10, wherein the activator is added in an amount of about 15% to about 80%, or from about 20% to about 80%, or from about 30% to about 75%, or from about 40% to about 75%, or from about 15% to about 50% of the total solvent volume contained in the silicone acrylic hybrid composition.

12. The method according to any one of items 1 to 11, wherein the activator has a boiling point which is higher than the boiling point of the solvent and has a vapor pressure at 20° C. which is lower than the vapor pressure of the solvent contained in the silicone acrylic hybrid composition.

13. The method according to any one of items 1 to 12, wherein the activator is selected from a volatile silicone, an aliphatic solvent, an aromatic solvent, a ketone, an aldehyde, an alcohol, an ester, a halogenated solvent, a mineral spirit, and combinations thereof.

14. The method according to any one of items 1 to 13, wherein the activator is selected from a silicone fluid, an aliphatic hydrocarbon, an acetate, a glycol, and combinations thereof.

15. The method according to any one of items 1 to 14, wherein the initial silicone acrylic hybrid composition contains a continuous, acrylic external phase and a discontinuous, silicone internal phase.

16. The method according to any one of items 1 to 15, wherein the solvent of the silicone acrylic hybrid composition is ethyl acetate.

17. The method according to any one of items 1 to 16, wherein the activator has a boiling point which is higher than the boiling point of ethyl acetate.

18. The method according to any one of items 1 to 17, wherein the activator has a vapor pressure at 20° C. which is lower than the vapor pressure of ethyl acetate.
19. The method according to any one of items 1 to 18, wherein the activator is selected from a volatile silicone, an aliphatic hydrocarbon, and combinations thereof.
20. The method according to any one of items 1 to 19, wherein the activator is selected from hexamethyldisiloxane, octamethyltrisiloxane, decamethyltetrasiloxane, n-heptane, n-octane, and combinations thereof.
21. The method according to any one of items 1 to 20, wherein the initial silicone acrylic hybrid composition contains a continuous, silicone external phase and a discontinuous, acrylic internal phase.
22. The method according to any one of items 1 to 14 and item 21, wherein the solvent of the silicone acrylic hybrid composition is n-heptane.
23. The method according to any one of items 1 to 14 and item 21 to 22, wherein the activator has a boiling point which is higher than the boiling point of n-heptane.
24. The method according to any one of items 1 to 14 and item 21 to 23, wherein the activator has a vapor pressure at 20° C. which is lower than the vapor pressure of n-heptane.
25. The method according to any one of items 1 to 14 and items 21 to 24 wherein the activator is selected from an ester, an alcohol, and combinations thereof.
26. The method according to any one of items 1 to 14 and items 21 to 25 wherein the activator is selected from propyl acetate, butyl acetate, ethylene glycol, propylene glycol, and combinations thereof.
27. The method according to any one of items 1 to 26, wherein the silicone acrylic hybrid pressure sensitive adhesive comprises the reaction product of the chemical reaction between a silicon-containing pressure sensitive adhesive composition comprising acrylate or methacrylate functionality, an ethylenically unsaturated monomer, and an initiator.
28. The method according to any one of items 1 to 27, wherein the silicone acrylic hybrid pressure sensitive adhesive comprises the reaction product of the chemical reaction between a silicon-containing pressure sensitive adhesive composition comprising acrylate or methacrylate functionality, a (meth)acrylate monomer, and an initiator.
29. The method according to any one of items 1 to 28, wherein the silicone acrylic hybrid composition is prepared by a method comprising the steps of:
(i) providing a silicon-containing pressure sensitive adhesive composition comprising acrylate or methacrylate functionality and the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE- where E is —O— or —NH— and A is an acryl group or a methacryl group,
    Y is a divalent alkylene radical having from 1 to 6 carbon atoms,
    W is a methyl or a phenyl radical,
    Z is a monovalent hydrolyzable organic radical or a halogen, and
    b is 0 or 1;
  wherein the silicone resin and silicone polymer are reacted to form a pressure sensitive adhesive, wherein the silicon-containing capping agent is introduced prior to, during, or after the silicone resin and silicone polymer are reacted, and wherein:
    the silicon-containing capping agent reacts with the pressure sensitive adhesive after the silicone resin and silicone polymer have been condensation reacted to form the pressure sensitive adhesive; or
    the silicon-containing capping agent reacts in-situ with the silicone resin and silicone polymer;
(ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
(iii) removing the first solvent; and
(iv) adding a second solvent to form the silicone acrylic hybrid composition, wherein the phase arrangement of the silicone acrylic hybrid composition is selectively controlled by selection of the second solvent.
30. The method according to any one of items 1 to 28, wherein the silicone acrylic hybrid composition is prepared by a method comprising the steps of:
(i) providing a silicon-containing pressure sensitive adhesive composition comprising acrylate or methacrylate functionality and the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE- where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to form a pressure sensitive adhesive, wherein the silicon-containing capping agent is introduced prior to, during, or after the silicone resin and silicone polymer are reacted, and wherein:
    the silicon-containing capping agent reacts with the pressure sensitive adhesive after the silicone resin and silicone polymer have been condensation reacted to form the pressure sensitive adhesive; or
    the silicon-containing capping agent reacts in-situ with the silicone resin and silicone polymer;
(ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
(iii) adding a processing solvent, wherein the processing solvent has a higher boiling point than the first solvent, and
(iv) applying heat at a temperature of from 70° C. to 150° C. such that a majority of the first solvent is selectively removed;
(v) removing the processing solvent; and.
(vi) adding a second solvent to form the silicone acrylic hybrid composition, wherein the phase arrangement of the silicone acrylic hybrid composition is selectively controlled by selection of the second solvent.
31. A pressure sensitive adhesive film or layer prepared by a method according to items 2 to 30.

32. A pressure sensitive adhesive film or layer prepared by a method according to items 2 to 30 having a continuous, silicone external phase and a discontinuous, acrylic internal phase or a continuous, acrylic external phase and a discontinuous, internal silicone phase.

33. A method of preparing a pressure sensitive adhesive film or layer having a continuous, silicone external phase and a discontinuous, acrylic internal phase based on a silicone acrylic hybrid composition which contains a continuous, acrylic external phase and a discontinuous, silicone internal phase, comprising the steps of:
  i) adding an activator to a silicone acrylic hybrid composition to provide an activator-containing pressure sensitive adhesive mixture, wherein the activator is optionally mixed with an active agent and optionally further excipients and/or additives before added to the silicone acrylic hybrid composition,
   the silicone acrylic hybrid composition comprising:
    a) a silicone acrylic hybrid pressure sensitive adhesive, and
    b) ethyl acetate, wherein the phase arrangement of the silicone phase and the acrylic phase in the initial silicone acrylic hybrid composition forming a continuous, acrylic external phase and a discontinuous, silicon internal phase is determined by ethyl acetate,
   wherein preferably the activator is added in an amount of at least 10% of the total solvent volume contained in the silicone acrylic hybrid composition, and
   wherein the activator
    a) is liquid at 20° C. and 1013 mbar,
    b) has a boiling point which is higher than the boiling point of ethyl acetate and/or has a vapor pressure at 20° C. which is lower than the vapor pressure of ethyl acetate, and
    c) provides better dissolution properties for the inner phase of the initial silicone acrylic hybrid composition than ethyl acetate,
  ii) coating said activator-containing pressure sensitive adhesive mixture on a film or release liner in an amount to provide the desired coating dry weight,
  iii) drying said coated activator-containing pressure sensitive adhesive mixture to provide a pressure sensitive adhesive film or layer with the desired coating dry weight.

34. A method of preparing a pressure sensitive adhesive film or layer having a continuous, silicone external phase and a discontinuous, acrylic internal phase based on a silicone acrylic hybrid composition which contains a continuous, acrylic external phase and a discontinuous, silicone internal phase, comprising the steps of:
  i) adding n-heptane, or silicone fluid to a silicone acrylic hybrid composition to provide a n-heptane or silicone fluid-containing pressure sensitive adhesive mixture, wherein n-heptane or the silicone fluid is optionally mixed with an active agent and optionally further excipients and/or additives before added to the silicone acrylic hybrid composition,
   the silicone acrylic hybrid composition comprising:
    a) a silicone acrylic hybrid pressure sensitive adhesive, and
    b) ethyl acetate, wherein the phase arrangement of the silicone phase and the acrylic phase in the initial silicone acrylic hybrid composition forming a continuous, acrylic external phase and a discontinuous, silicon internal phase is determined by the ethyl acetate,
   wherein preferably the n-heptane or the silicone fluid is added in an amount of at least 10% of the total solvent volume contained in the silicone acrylic hybrid composition,
  ii) coating said n-heptane or silicone fluid-containing pressure sensitive adhesive mixture on a film or release liner in an amount to provide the desired coating dry weight,
  iii) drying said coated n-heptane or silicone fluid-containing pressure sensitive adhesive mixture to provide a pressure sensitive adhesive film or layer with the desired coating dry weight.

35. A method of preparing a pressure sensitive adhesive film or layer having a continuous, acrylic external phase and a discontinuous, silicone internal phase based on a silicone acrylic hybrid composition which contains a continuous, silicone external phase and a discontinuous, acrylic internal phase, comprising the steps of:
  i) adding an activator to a silicone acrylic hybrid composition to provide an activator-containing pressure sensitive adhesive mixture, wherein the activator is optionally mixed with an active agent and optionally further excipients and/or additives before added to the silicone acrylic hybrid composition,
   the silicone acrylic hybrid composition comprising:
    a) a silicone acrylic hybrid pressure sensitive adhesive, and
    b) n-heptane, wherein the phase arrangement of the silicone phase and the acrylic phase in the initial silicone acrylic hybrid composition forming a continuous, silicone external phase and a discontinuous, acrylic internal phase is determined by n-heptane,
   wherein preferably the activator is added in an amount of at least 10% of the total solvent volume contained in the silicone acrylic hybrid composition, and
   wherein the activator
    a) is liquid at 20° C. and 1013 mbar,
    b) has a boiling point which is higher than the boiling point of n-heptane and/or has a vapor pressure at 20° C. which is lower than the vapor pressure of n-heptane, and
    c) provides better dissolution properties for the inner phase of the initial silicone acrylic hybrid composition than the n-heptane,
  ii) coating said activator-containing pressure sensitive adhesive mixture on a film or release liner in an amount to provide the desired coating dry weight,
  iii) drying said coated activator-containing pressure sensitive adhesive mixture to provide a pressure sensitive adhesive film or layer with the desired coating dry weight.

36. A method of preparing a pressure sensitive adhesive film or layer having a continuous, acrylic external phase and a discontinuous, silicone internal phase based on a silicone acrylic hybrid composition which contains a continuous, silicone external phase and a discontinuous, acrylic internal phase, comprising the steps of:
  i) adding propyl acetate or butyl acetate to a silicone acrylic hybrid composition to provide a propyl acetate or butyl acetate-containing pressure sensitive adhesive mixture, wherein the propyl acetate or the butyl acetate is optionally mixed with an active agent and optionally further excipients and/or additives before added to the silicone acrylic hybrid composition, the silicone acrylic hybrid composition comprising:
a) a silicone acrylic hybrid pressure sensitive adhesive, and
b) n-heptane, wherein the phase arrangement of the silicone phase and the acrylic phase in the initial silicone acrylic hybrid composition forming a continuous, silicone external phase and a discontinuous, acrylic internal phase is determined by n-heptane, wherein preferably the propyl acetate or the butyl acetate is added in an amount of at least 10% of the total solvent volume contained in the silicone acrylic hybrid composition,
ii) coating said propyl acetate or butyl acetate-containing pressure sensitive adhesive mixture on a film or release liner in an amount to provide the desired coating dry weight,
iii) drying said coated propyl acetate or butyl acetate-containing pressure sensitive adhesive mixture to provide a pressure sensitive adhesive film or layer with the desired coating dry weight.

37. A transdermal drug delivery system comprising a pressure sensitive adhesive film or layer prepared by a method according to items 3 to 36.

38. A method of inverting the phase arrangement of the silicone phase and the acrylic phase in a silicone acrylic hybrid composition,
the silicone acrylic hybrid composition comprising:
a) a silicone acrylic hybrid pressure sensitive adhesive, and
b) ethyl acetate, wherein the phase arrangement of the silicone phase and the acrylic phase in the initial silicone acrylic hybrid composition forming a continuous, acrylic external phase and a discontinuous, silicone internal phase is determined by ethyl acetate,
comprising the step of adding an activator to the silicone acrylic hybrid composition, preferably in an amount of at least 10% of the total solvent volume contained in the silicone acrylic hybrid composition, wherein the activator
a) is liquid at 20° C. and 1013 mbar,
b) has a boiling point which is higher than the boiling point of ethyl acetate and/or has a vapor pressure at 20° C. which is lower than the vapor pressure of ethyl acetate, and
c) provides better dissolution properties for the inner phase of the initial silicone acrylic hybrid composition than the ethyl acetate.

39. A method of inverting the phase arrangement of the silicone phase and the acrylic phase in a silicone acrylic hybrid composition,
the silicone acrylic hybrid composition comprising:
a) a silicone acrylic hybrid pressure sensitive adhesive, and
b) n-heptane, wherein the phase arrangement of the silicone phase and the acrylic phase in the initial silicone acrylic hybrid composition forming a continuous, silicone external phase and a discontinuous, acrylic internal phase is determined by n-heptane,
comprising the step of adding an activator to the silicone acrylic hybrid composition, preferably in an amount of at least 10% of the total solvent volume contained in the silicone acrylic hybrid composition, wherein the activator
a) is liquid at 20° C. and 1013 mbar,
b) has a boiling point which is higher than the boiling point of n-heptane and/or has a vapor pressure at 20° C. which is lower than the vapor pressure of n-heptane, and
c) provides better dissolution properties for the inner phase of the initial silicone acrylic hybrid composition than the n-heptane.

The invention claimed is:

1. A method of inverting the phase arrangement of the silicone phase and the acrylic phase in a silicone acrylic hybrid composition,
the silicone acrylic hybrid composition comprising:
a) a silicone acrylic hybrid pressure sensitive adhesive, and
b) a solvent, wherein the phase arrangement of the silicone phase and the acrylic phase in the initial silicone acrylic hybrid composition forming a continuous external phase and a discontinuous internal phase is determined by the solvent,
comprising the step of adding an activator to the silicone acrylic hybrid composition, wherein the activator
a) is liquid at 20° C. and 1013 mbar,
b) has a boiling point which is higher than the boiling point of the solvent and/or has a vapor pressure at 20° C. which is lower than the vapor pressure of the solvent contained in the silicone acrylic hybrid composition, and
c) provides better dissolution properties for the inner phase of the initial silicone acrylic hybrid composition than the solvent contained in the silicone acrylic hybrid composition.

2. A method of preparing a pressure sensitive adhesive film or layer based on a silicone acrylic hybrid composition comprising the steps of:
i) adding an activator to a silicone acrylic hybrid composition to provide an activator-containing pressure sensitive adhesive mixture,
the silicone acrylic hybrid composition comprising:
a) a silicone acrylic hybrid pressure sensitive adhesive, and
b) a solvent, wherein the phase arrangement of the silicone phase and the acrylic phase in the initial silicone acrylic hybrid composition forming a continuous external phase and a discontinuous internal phase is determined by the solvent,
wherein the activator
a) is liquid at 20° C. and 1013 mbar,
b) has a boiling point which is higher than the boiling point of the solvent and/or has a vapor pressure at 20° C. which is lower than the vapor pressure of the solvent contained in the silicone acrylic hybrid composition, and
c) provides better dissolution properties for the inner phase of the initial silicone acrylic hybrid composition than the solvent contained in the silicone acrylic hybrid composition,
ii) coating said activator-containing pressure sensitive adhesive mixture on a film or release liner in an amount to provide the desired coating dry weight,
iii) drying said coated activator-containing pressure sensitive adhesive mixture to provide a pressure sensitive adhesive film or layer with the desired coating dry weight.

3. The method according to claim 2, wherein in step i) the activator is mixed with an active agent and optionally further excipients and/or additives before added to the silicone acrylic hybrid composition.

4. The method according to claim 3, wherein the active agent is insoluble or has a limited solubility at 20° C. in the silicone acrylic hybrid composition and/or the activator.

5. The method according to claim 3, wherein the active agent is felodipine.

6. The method according to claim 2, wherein the silicone acrylic hybrid composition further comprises a non-hybrid pressure sensitive adhesive based on polysiloxanes or acrylates.

7. The method according to claim 2, wherein the activator is added in an amount of at least 10%, at least 15%, or at least 20% of the total solvent volume contained in the silicone acrylic hybrid composition.

8. The method according to claim 2, wherein the activator is selected from a volatile silicone, an aliphatic solvent, an aromatic solvent, a ketone, an aldehyde, an alcohol, an ester, a halogenated solvent, a mineral spirit, and combinations thereof.

9. The method according to claim 2, wherein the initial silicone acrylic hybrid composition contains a continuous, acrylic external phase and a discontinuous, silicone internal phase.

10. The method according to claim 2 wherein the solvent of the silicone acrylic hybrid composition is ethyl acetate and the activator has a boiling point which is higher than the boiling point of ethyl acetate and/or has a vapor pressure at 20° C. which is lower than the vapor pressure of ethyl acetate.

11. The method according to claim 2, wherein the activator is selected from a volatile silicone, an aliphatic hydrocarbon, and combinations thereof.

12. The method according to claim 2, wherein the activator is selected from hexamethyldisiloxane, octamethyltrisiloxane, decamethyltetrasiloxane, n-heptane, n-octane, and combinations thereof.

13. The method according to claim 2, wherein the initial silicone acrylic hybrid composition contains a continuous, silicone external phase and a discontinuous, acrylic internal phase.

14. The method according to claim 2 wherein the solvent of the silicone acrylic hybrid composition is n-heptane and the activator has a boiling point which is higher than the boiling point of n-heptane and/or has a vapor pressure at 20° C. which is lower than the vapor pressure of n-heptane.

15. The method according to claim 2, wherein the activator is selected from an ester, an alcohol, and combinations thereof.

16. The method according to claim 2, wherein the activator is selected from propyl acetate, butyl acetate, ethylene glycol, propylene glycol, and combinations thereof.

17. The method according to claim 2, wherein the silicone acrylic hybrid pressure sensitive adhesive comprises the reaction product of the chemical reaction between a silicon-containing pressure sensitive adhesive composition comprising acrylate or methacrylate functionality, an ethylenically unsaturated monomer, and an initiator.

18. The method according to claim 2, wherein the silicone acrylic hybrid composition is prepared by a method comprising the steps of:
(i) providing a silicon-containing pressure sensitive adhesive composition comprising acrylate or methacrylate functionality and the condensation reaction product of:
a silicone resin,
a silicone polymer, and
a silicon-containing capping agent which provides said acrylate or methacrylate functionality, wherein said silicon-containing capping agent is of the general formula $XYR'_bSiZ_{3-b}$, wherein
X is a monovalent radical of the general formula AE- where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure sensitive adhesive, wherein the silicon-containing capping agent is introduced prior to, during, or after the silicone resin and silicone polymer are reacted, and wherein:
the silicon-containing capping agent reacts with the pressure sensitive adhesive after the silicone resin and silicone polymer have been condensation reacted to form the pressure sensitive adhesive; or
the silicon-containing capping agent reacts in-situ with the silicone resin and silicone polymer;
(ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
(iii) removing the first solvent; and
(iv) adding a second solvent to form the silicone acrylic hybrid composition, wherein the phase arrangement of the silicone acrylic hybrid composition is selectively controlled by selection of the second solvent.

* * * * *

UNITED STATES PATENT AND TRADEMARK OFFICE
CERTIFICATE OF CORRECTION

| | |
|---|---|
| PATENT NO. | : 11,198,800 B2 |
| APPLICATION NO. | : 16/318430 |
| DATED | : December 14, 2021 |
| INVENTOR(S) | : Marco Emgenbroich et al. |

It is certified that error appears in the above-identified patent and that said Letters Patent is hereby corrected as shown below:

In the Specification

In Column 9, Line 53, delete "total" and insert -- form --, therefor.

In Column 19, under "TABLE 2", Line 5, "fuid" should read -- fluid --.

In Column 23, Line 61, delete "W" and insert -- R' --, therefor.

Signed and Sealed this
Seventh Day of February, 2023

Katherine Kelly Vidal
*Director of the United States Patent and Trademark Office*